United States Patent [19]

Bagli et al.

[11] Patent Number: 4,786,640
[45] Date of Patent: Nov. 22, 1988

[54] 2,6-DISUBSTITUTED-5-CYANO-4-PYRIMIDINYLOXYACETIC ACID ALDOSE REDUCTASE INHIBITORS

[75] Inventors: Jehan F. Bagli; John W. Ellingboe, both of Princeton; Thomas R. Alessi, Flemington, all of N.J.

[73] Assignee: American Home Products Corporation, New York, N.Y.

[21] Appl. No.: 62,734

[22] Filed: Jun. 12, 1987

[51] Int. Cl.$^4$ .................. A61K 31/505; C07D 239/02
[52] U.S. Cl. ..................................... 514/269; 544/319
[58] Field of Search ......................... 544/319; 514/269

[56]       References Cited
       U.S. PATENT DOCUMENTS

| 4,234,587 | 11/1980 | Maurer et al. | 544/319 |
| 4,505,910 | 3/1985 | Bagli | 514/26 |
| 4,568,693 | 2/1986 | Sestanj | 514/524 |
| 4,617,393 | 10/1986 | Bagli | 544/319 |

OTHER PUBLICATIONS

Noller, Textbook of Organic Chemistry, 3rd edition, W. B. Saunders Co., Philadelphia, 1966, pp. 139, 173.
Wolff, Burger's Medicinal Chemistry, 4th Ed., Part II, 1979, John Wiley & Sons, New York, pp. 1049–1057.

Primary Examiner—Alan L. Rotman
Assistant Examiner—Robert C. Whittenbaugh
Attorney, Agent, or Firm—Walter Patton

[57]         ABSTRACT

Disclosed herein are 2,6-disubstituted-5-cyano-4-pyrimidinyloxyacetic acids and pharmaceutically acceptable salts thereof and methods of their preparation. The compounds are new aldose reductase inhibitors useful for the treatment or prevention of diabetic complications.

7 Claims, No Drawings

2,6-DISUBSTITUTED-5-CYANO-4-PYRIMIDINYLOXYACETIC ACID ALDOSE REDUCTASE INHIBITORS

BACKGROUND OF THE INVENTION

This invention relates to 2,6-disubstituted-5-cyano-4-pyrimidinyloxyacetic acids, to pharmaceutical salts thereof, to the processes for their preparation, and to methods for using these compounds. The compounds have pharmaceutical properties which render them beneficial for the treatment or prevention of diabetic complications.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts, and atherosclerosis. These complications have been linked to the undesirable accumulation of sorbitol in diabetic tissue, which in turn results from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators (see J. H. Kinoshita et al, Biochem. Biophys. Acta, 158, 472 (1968) and references cited therein) have demonstrated that aldose reductase plays a central role in the etiology of galactosemic cataracts by effecting the conversion of galactose to dulcitol (galactitol); and that an agent capable of inhibiting aldose reductase can prevent the detrimental accumulation of dulcitol in the lens. Furthermore, a relationship between elevated levels of glucose and an undesireable accumulation of sorbitol has been demonstrated in the lens, peripheral nervous cord, and kidney of diabetic animals, (see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970)).

N-[[6-Methoxy-5-(trifluoromethyl)-1-naphthalenyl]-thioxomethyl]-N-methylglycine has been reported to be an effective inhibitor of aldose reductase, see K. Sestanj et al, U.S. Pat. No. 4,568,693, Feb. 4, 1986. The present invention discloses novel 2,6-disubstituted-5-cyano-4-pyrimidinyloxyacetic acids which unexpectedly show aldose reductase inhibitory activity. Up to now, aminopyrimidine derivatives have been reported to be useful for increasing cardiac contractility, see J. Bagli et al, U.S. Pat. Nos. 4,505,910, Mar. 19, 1985, and 4,617,393, Oct. 14, 1986.

SUMMARY OF THE INVENTION

The 2,6-disubstituted-5-cyano-4-pyrimidinyloxyacetic acid of this invention are represented by formula (I)

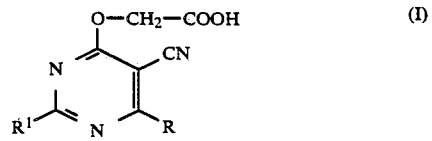

wherein $R^1$ is lower alkyl containing 1 to 6 carbon atoms, cyclo(lower)alkyl containing 3 to 6 carbon atoms, phenyl, halogen substituted phenyl, phenylmethyl, naphthalenyl, halogen substituted naphthalenyl, or thienyl; R is $-SR^2$ wherein $R^2$ is lower alkyl containing 1 to 6 carbon atoms, lower cycloalkylmethyl containing 4 to 7 carbon atoms, phenylmethyl, or halogen substituted phenylmethyl; or R is $R^3$ wherein $R^3$ is lower alkyl containing 1 to 4 carbon atoms, phenyl, or 1-naphthalenylmethyl; and the pharmaceutically acceptable salts thereof.

A preferred aspect of the present invention is the compounds of formula (I) wherein $R^1$ is 1-methylethyl, 1,1-dimethylethyl, propyl, 2,2-dimethylpropyl, phenyl, 4-bromophenyl, naphthalenyl, 5-bromonaphthalenyl, or 2-thienyl; R is $-SR^2$ wherein $R^2$ is methyl, 1-methylethyl, hexyl, cyclohexylmethyl, phenylmethyl, 4-bromophenylmethyl, or 4-bromo-2-fluorophenylmethyl; or R is $R^3$ wherein $R^3$ is methyl, 1-methylethyl, phenyl, or 1-naphthalenylmethyl; and the pharmaceutically acceptable salts thereof.

A still further preferred aspect of the present invention is the compounds of formula (I) wherein $R^1$ is 1,1-dimethylethyl or 5-bromonaphthalenyl; R is $-SR^2$ wherein $R^2$ is methyl, hexyl, cyclohexylmethyl, or phenylmethyl; or R is $R^3$ wherein $R^3$ is 1-naphthalenylmethyl; and the pharmaceutically acceptable salts thereof.

The most preferred compounds of the present invention are [[5-cyano-6-[(cyclohexylmethyl)thio]-2-(1,1-dimethylethyl)-4-pyrimidinyl]oxy]acetic acid; and [[2-(5-bromo-1-naphthalenyl)-5-cyano-6-[(1-naphthalenyl)methyl]-4-pyrimidinyl]oxy]acetic acid; and the pharmaceutically acceptable salts thereof.

The 2,6-disubstituted-5-cyano-4-pyrimidinyloxyacetic acids, and the pharmaceutically acceptable salts thereof can be prepared by the processes described hereinafter.

A method is provided for preventing or relieving diabetes mellitus associated complications in a diabetic mammal by administering to said mammal a prophylactic or alleviating amount of a compound of formula (I). Such complications include neuropathy, nephropathy, retinopathy, and cataracts.

The compounds of formula (I), when admixed with a pharmaceutically acceptable carrier, form a pharmaceutical composition which can be used according to the preceding method.

DETAILED DESCRIPTION OF THE INVENTION

The compounds of formula (I) form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates, or bicarbonates of the therapeutically acceptable alkali metals or alkaline earth metals, for example, sodium, potassium, magnesium, calcium, and the like. Suitable organic bases include the following amines: benzylamine; lower mono-, di- ior trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine, and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example, tetramethyl), alkyl-alkanol (for example, methyltriethanol and trimethyl-monoethanol), and cyclic ammonium salts, for example, the N-methylpyridinium, N-methyl-N-(2-hydroxyethyl)-morpholinium, N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate, or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula (I) is dissolved in a suitable solvent of either moderate or low polarity, for example, ethanol, methanol, ethyl acetate, diethyl ether, and benzene. At least an equivalent amount of the amine corresponding to the desired cation is then added to that solution. If the resulting salt does not precipitate, it can usually be obtained in solid form by addition of a miscible diluent off lower polarity, for example, benzene or petroleum ether, or by evaporation. If the amine is relatively volatile, any excess can easily be removed by evaporation. It is preferred to use essentially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

The 2,6-disubstituted-5-cyano-4-pyrimidinyloxyacetic acids and the pharmaceutically acceptable salts thereof of this invention may be administered to mammals, for example, man, monkeys, or dogs, either alone or combined with pharmaceutically acceptable excipients, in dosage forms, i.e., capsules or tablets.

Preferably, the compounds of this invention may be given orally. However, the method of administering the present active ingredients of this invention is not to be construed as limited to a particular mode of administration. For example, the compounds may be administered topically directly in the eye in the form of drops of sterile, buffered ophthalmic solutions, preferably of pH 7.2–7.6. Also, they may be administered orally in solid form containing such excipients as starch, milk sugar, certain types of clay, and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the 2,6-disubstituted-5-cyano-4-pyrimidinyloxyacetic acids and the pharmaceutically acceptable salts thereof will vary with the form of administration. Furthermore, it will vary with the particular host under treatment. Generally, treatment is initiated with small dosages substantially less than the optimal dose of the compound. In general, the compounds of this invention are most desirably administered at a concentration level that will generally afford effective results without causing any harmful or deleterious side effects. For topical administration, a 0.05–1.8% solution may be administered dropwise in the eye. The frequency of instillation varies with the subject under treatment from a drop every two or three days to once daily. For oral or parenteral administration a preferred level of dosage ranges from about 0.5 mg to about 1000 mg per kilo of body weight per day, although aforementioned variations will occur. However, a dosage level that is in the range of from about 5.0 mg to about 60 mg per kilo of body weight per day is most satisfactory.

Unit dosage forms such as capsules, tablets, pills, and the like may contain from about 25 mg to about 1250 mg of the active ingredients of this invention with a pharmaceutical carrier. Thus, for oral administration, capsules can contain from between about 25 mg to about 1250 mg of the active ingredients of this invention with or without a pharmaceutical diluent. Tablets, either effervescent or noneffervescent, can contain between about 25 to 1250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents, for example, starch.

The 2,6-disubstituted-5-cyano-4-pyrimidinyloxyacetic acids and the pharmaceutically acceptable salts thereof can also be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide, and phenformin, are suitable. The compounds herein can be administered sequentially or simultaneously with insulin or the oral hypoglycemic agent. Suitable methods of administration, compositions, and doses of the insulin preparation or oral hypoglycemic agent are described in medical textbooks; for instance, "Physicians' Desk Reference", 36 ed., Medical Economics Co., Oradell, N.J. U.S.A., 1982. When used in combination, the 2,6-disubstituted-5-cyano-4-pyrimidinyloxyacetic acids and the pharmaceutically acceptable salts thereof are administered as described previously. The 2,6-disubstituted-5-cyano-4-pyrimidinyloxyacetic acids and the pharmaceutically acceptable salts thereof can be administered with an oral hypoglycemic agent in the form of a pharmaceutical composition comprising effective amounts of each agent.

The aldose reductase inhibiting property of the compounds of this invention and the utilization of the compounds in preventing, diminishing, and alleviating diabetic complications are demonstrable in experiments using galactosemic rats, see Dvornik et al, Science, 182, 1146 (1973). Such experiments are exemplified hereinbelow after the listing of the following general comments pertaining to these experiments.

Male Sprague-Dawley rats, weighing approximately 90 grams were separated into groups of equal average body weight, with six animals per group. The animals were housed in cages of six animals each and maintained on 12 hour night/12 hour day cycles. Except as otherwise noted, the animals were given food and water ad libitum.

On day 1, the galactosemic control group and all drug-treated groups were given access to 20% galactose chow (Bio-Serv, Frenchtown, NJ). Animals in the control group were given access to 20% glucose chow (Bio-Serv). Test compounds were administered either in the diet or by gavage as a suspension in 2% Tween 80 in saline. In experiments in which gavage dosing was used, the animals were administered the test compound daily at approximately the same hour each day. Food intake and body weight were determined twice during the course of the experiment. In cases in which the compound was administered in the diet, the average dose was calculated on the basis of the actual average food intake during the experiment.

On the morning of day 5, all animals were fasted; beginning two hours later the animals were decapitated and the lenses, sciatic nerves, and a 50-100 mg portion of the diaphragm were removed, weighed, and frozen in porcelain plates on dry ice.

The polyol determination was performed by a modification of the procedure of M. Kraml et al, Clin. Biochem., 2, 373 (1969). Only two minor reagent changes were made: (a) the rinsing mixture was an aqueous 5% (w/v) trichloroacetic acid solution and (b) the stock solution was prepared by dissolving 25 mg of dulcitol in 100 mL of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.]

The aldose reductase inhibiting effects of the compounds of formula (I) were also tested by employing an in vitro testing procedure similar to that described by S. Hayman and J. H. Kinoshita, J. Biol. Chem., 240, 877 (1965). In the present case the procedure of Hayman and Kinoshita was modified in that the final chromatography step was omitted in the preparation of the enzyme from bovine lens.

The following tabulated results show that the 2,6-disubstituted-5-cyano-4-pyrimidinyloxyacetic acids of this invention show the property that they diminish the accumulation of galactitol in the lenses and sciatic nerves of rats fed galactose. The figures under L, N and D represent the percentage decrease of galactitol accumulation in the tissues of the lens, sciatic nerve, and diaphragm, respectively, for treated rats as compared to untreated rats.

The last entry in the tables is the compound N-[[6-methoxy-5-(trifluoromethyl)-1-naphthalenyl]-thioxomethyl]-N-methylglycine. The latter compound is also known as tolrestat. (See U.S. Pat. No. 4,568,693.)

TABLE 1

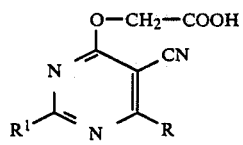

| Test Compound Example No. | $R^1$ | R | % Inhibition IN VITRO | | | % Lowering dulcitol accumulation IN VIVO | | | | Melting Point °C. |
|---|---|---|---|---|---|---|---|---|---|---|
| | | | $10^{-5}$ M | $10^{-6}$ M | $10^{-7}$ M | mg/kg | L | N | D | |
| 1 | t-butyl | —S—CH₂—cyclohexyl | 97 | 96 | 88 | 105 | — | 70 | 60 | 126–128 |
| 2 | t-butyl | —S—CH₂—(3-F,4-Br-phenyl) | 98 | 93 | 93 | 99 | — | 28 | 47 | 154–155 |
| 3 | t-butyl | —SCH₃ | 89 | 88 | 82 | 83 | — | 35 | 32 | 212–215 |
| 4 | t-butyl-CH₂— | —SCH₃ | 95 | 96 | 85 | 98 | — | — | 22 | 155–157 |
| 5 | i-propyl | —SCH₃ | 98 | 97 | 88 | 78 | — | 37 | — | 158–160 |
| 6 | —CH₂—phenyl | —SCH₃ | 91 | 90 | 78 | 76 | — | — | — | 171–173 |
| 7 | n-propyl | —SCH₃ | 92 | 89 | 74 | 78 | — | — | — | 160–162 |

TABLE 1-continued

Structure (I):
$$\text{Pyrimidine with } O\text{-}CH_2\text{-}COOH, CN, R^1, R \text{ substituents}$$

| Test Compound Example No. | R¹ | R | % Inhibition IN VITRO $10^{-5}$ M | % Inhibition IN VITRO $10^{-6}$ M | % Inhibition IN VITRO $10^{-7}$ M | % Lowering dulcitol accumulation IN VIVO mg/kg | L | N | D | Melting Point °C |
|---|---|---|---|---|---|---|---|---|---|---|
| 8 | methylcyclohexyl | —S—CH₂—phenyl | 95 | 91 | 73 | 117 | — | — | — | 182–183 |
| 9 | p-Br-phenyl | —SCH₃ | 95 | 93 | 82 | 114 | — | — | 27 | 233–235 |
| 10 | t-butyl | —S—CH₂—phenyl-Br | 95 | 95 | 95 | 135 | — | — | 58 | 160–162 |
| 11 | t-butyl | —S—nC₆H₁₃ | 94 | 94 | 91 | 112 | — | 43 | 60 | 91–92 |
| 12 | t-butyl | —S—i-propyl | 92 | 91 | 89 | 82 | — | 37 | 19 | 120–122 |
| 13 | —CH₃ | —SCH₃ | 90 | 84 | 55 | 79 | — | — | — | 205–206 |
| 14 | methylphenyl | —SCH₃ | 92 | 87 | 75 | 96 | — | — | 55 | 223–224 |
| 15 | methylcyclohexyl | —SCH₃ | 90 | 90 | 74 | 91 | — | — | — | 149–150 |
| 16 | t-butyl | —S—CH₂—phenyl | 86 | 85 | 82 | 97 | — | 46 | 67 | 126–129 |
| 17 | thienyl | —SCH₃ | 98 | 97 | 92 | 90 | — | — | — | 211–215 |

The compounds of Table 1 are produced by Process 1 set forth below.

TABLE 2

Structure (I):
$$\text{Pyrimidine with } O\text{-}CH_2\text{-}COOH, CN, R^1, R \text{ substituents}$$

| Test Compound Example No. | R¹ | R | % Inhibition IN VITRO $10^{-5}$ M | % Inhibition IN VITRO $10^{-6}$ M | % Inhibition IN VITRO $10^{-7}$ M | % Lowering dulcitol accumulation IN VIVO mg/kg | L | N | D | Melting Point °C |
|---|---|---|---|---|---|---|---|---|---|---|
| 1 | 5-Br—naphthalenyl | 1-naphthalenylmethyl | 90 | 85 | 46 | 166 | — | — | — | 236–237(dec.) |
| 2 | methylphenyl | —CH₃ | 92 | 88 | 79 | 78 | — | — | — | 228–229 |
| 3 | 1-naphthyl | —CH₃ | 93 | 85 | 46 | 83 | — | — | — | 198–199 |

TABLE 2-continued

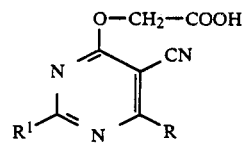
(I)

| Test Compound Example No. | R¹ | R | % Inhibition IN VITRO $10^{-5}$ M | $10^{-6}$ M | $10^{-7}$ M | % Lowering dulcitol accumulation IN VIVO mg/kg | L | N | D | Melting Point °C. |
|---|---|---|---|---|---|---|---|---|---|---|
| 4 | phenyl | phenyl | 96 | 94 | 85 | 100 | 17 | — | — | 221–222 |
| 5 | 1-naphthalenyl | phenyl | 79 | 76 | 53 | 112 | — | — | — | 187–188 |
| 6 | 5-Br—naphthalenyl | i-propyl | 94 | 90 | 53 | 120 | — | — | — | 209.5–210.5 |
| N—[[6-methoxy-5-(trifluoromethyl)-1-naphthalenyl]-thioxomethyl]-N—methylglycine(tolrestat) U.S. Pat. No. 4,568,693 | | | 98 | 94 | 65 | 6 | N.S. | 53 | 90 | 164–165 |

The compounds of Table 2 are produced by Process 2 set forth below.
N.S. = not significant

THE PROCESS

The 2,6-disubstituted-5-cyano-4-pyrimidinyloxyacetic acids of the present invention were produced by Process 1, condensation of suitable amidines (III) with β,β-bisthioalkyl-α-cyanoacrylic acid methyl esters (VI) to produce pyrimidines (VII); and Process 2, condensation of cyanoacetamide (XIV) with N-acyliminoethers (XIII) to produce the pyrimidines (XV). O-Alkylations of (VII) and (XV) were carried out with X—CH₂COOR⁴ wherein R⁴ is lower alkyl, and X is bromine or iodine; preferably with methyl or t-butyl bromoacetates to produce the pyrimidine esters (VIII) and (XVI); and finally hydrolysis of (VIII) and (XVI) to the desired compounds of formula (I).

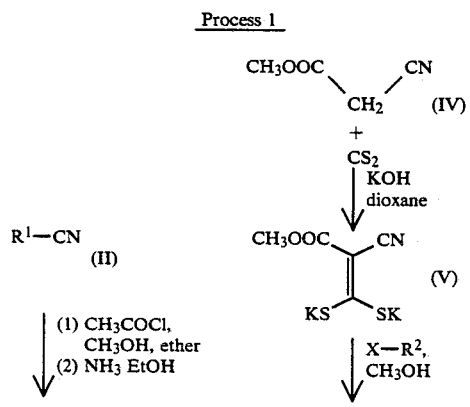

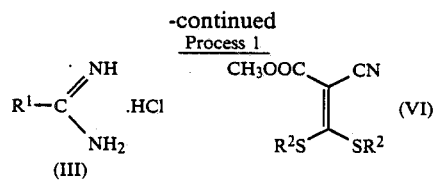

wherein R¹ and R² are as defined above; R⁴ is lower alkyl containing 1 to 4 carbon atoms; and X is bromine, or iodine.

Process 2

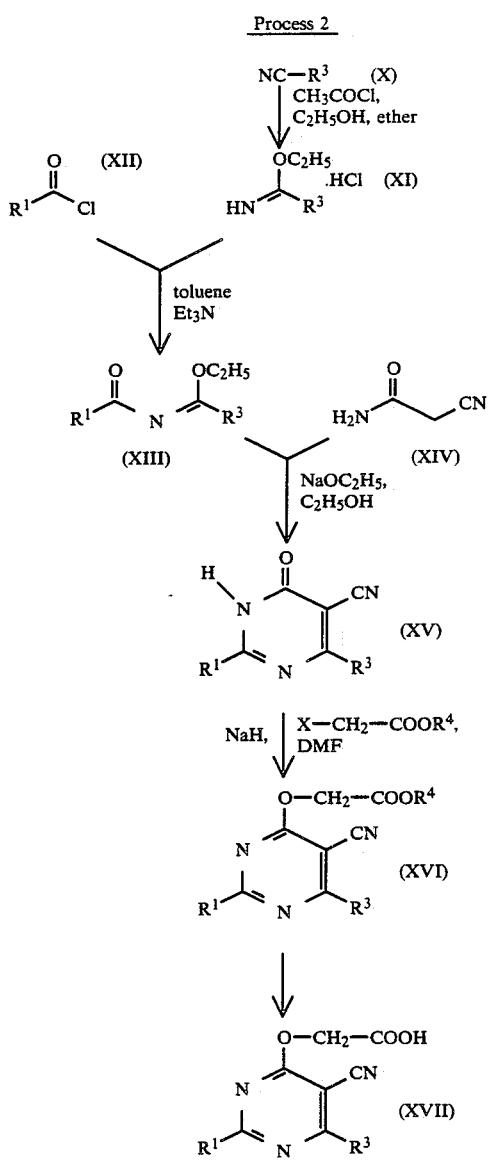

wherein $R^1$, $R^3$, $R^4$, and X are as defined above.

Referring to Process 1, the required amidines (III) were obtained from the corresponding nitriles (II) in two steps via iminoethers as described in P. E. Fanta et al, J. Am. Chem. Soc., 78, 1434 (1956). However, preparation of naphthalenyl amidine as reported in L. Weintraub, J. Org. Chem., 33, 1679 (1968), via the iminoether of naphthalenyl-1-carboxamide was not reproducible in our hands. The reaction yielded either the starting material or naphthalenyl-1-carbonitrile. The naphthalene moiety was introduced using the alternative synthesis described in Process 2. The required β,β-bisthioalkyl-α-cyanoacrylic acid methyl esters (VI) in Process 1 were prepared using the general process reported in K. A. Jensen et al, Acta Chem. Scand., 22, 1107 (1968), for the reaction of carbon disulfide with active methylene containing compounds (IV) to produce the compounds (V), followed by alkylation.

Referring to Process 2, the nitriles (X) were transformed to the corresponding iminoethers (XI). Condensation of these iminoethers (XI) with an acyl chloride (XII) led to the N-acylimidates (XIII). These compounds, on condensation with cyanoacetamide (XIV), according to J. L. Soto et al, J. Chem. Soc. Perkins Trans I., 2447 (1984), led to suitably substituted pyrimidines (XV).

In both Process 1 and 2, alkylation of pyrimidines (VII) and (XV), respectively, was effected using sodium hydride as a base in the presence of suitable solvents. It was observed that the proportion of N- and O-alkylated products can be controlled by the choice of the solvent used for the reaction. Thus, using tetrahydrofuran (THF), or dimethoxyethane (DME), it was possible to preferentially obtain N-alkylation, whereas use of dimethylformamide (DMF) as a solvent led to O-alkylation as a preponderant product.

The alkylation could be affected either by using methyl bromoacetate or t-butyl bromoacetate.

The structures of the products of formula (I) was assigned based on the following observations.

(1) The infrared spectra showed only one carbonyl absorption band at 1720–1740 cm$^{-1}$ due to the carboxylic acid carbonyl.

(2) The —O—CH$_2$—signal characteristic in the NMR.

(3) The higher $R_f$ on the thin layer chromatography relative to the N-alkylated isomers.

The following Examples further illustrate this invention.

EXAMPLE 1

(Process 1)

[[5-Cyano-6-[(cyclohexylmethyl)thio]-2-(1,1-dimethylethyl)-4-pyrimidinyl]oxy]acetic Acid

[(I): $R^1$=t-butyl; R=(cyclohexylmethyl)thio]

Step (1) Preparation of t-Butyl Amidine Hydrochloride

To a cooled (0° C.), magnetically stirred solution of 2,2-dimethyl-1-propanenitrile (25.0 g, 0.30 mol), dry methanol (26.8 mL, 0.79 mol), and ether (30 mL) was added acetyl chloride (25.7 mL, 0.36 mol) dropwise. After the addition, cooling was continued for 15 minutes. The mixture was stirred at room temperature for 3 days. The resulting white crystals were filtered, washed with ether, and dried in vacuo. After drying, the crystals were combined with 10% NH$_3$/ethanol (150 mL, 0.90 mol), and stirred at room temperature for 3 days. The solution was filtered, and the filtrate was concentrated to give a white solid. Recrystallization from ethanol yielded white crystals (18.9 g, 46%), m.p. 188°–190° C.

NMR (DMSO-d$_6$): δ1.22 (s, 9H), 8.63 (br d, 3H).

Step (2) Preparation of Methyl 3,3-Dithio-2-cyano-2-propenoate Dipotassium Salt

According to the procedure of K. A. Jensen et al, Acta Chem. Scand., 22, 1107 (1968), to a cooled (20° C.), stirred suspension of powdered KOH (10.0 g, 0.18 mol) in dioxane (50 mL) was added a solution of methyl cyanoacetate (7.9 mL, 0.09 mol), and carbon disulfide (5.4 mL, 0.09 mol) in dioxane (30 mL) dropwise over 30 minutes. The cooling bath was removed and stirring was continued for 1 hour. Ether (75 mL) was added and the reaction mixture was filtered. The collected solid was washed with 1:1 dioxane/ether (100 mL), and dried over P$_2$O$_5$ in vacuo to yield a yellow powder (15.7 g, 70%). The product was used without further purification.

NMR (DMSO-d$_6$): δ4.15 (s, 3H).

Step (3) Preparation of Methyl 3,3-Bis(cyclohexylmethylthio)-2-cyano-2-propenoate To a stirred solution of methyl 3,3-dithio-2-cyano-2-propenoate dipotassium salt (17.8 g, 0.07 mol) in water (50 mL) was added a solution of bromomethylcyclohexane (19.8 mL, 0.14 mol) in ethanol (100 mL). The resulting solution was heated at reflux for 5 hours, concentrated, and diluted with water. The mixture was extracted with ethyl acetate, and the combined extracts were dried (MgSO$_4$) and concentrated. Purification of the crude product by flash column chromatography (eluant, 5% ethyl acetate/hexane) gave a yellow oil (16.4 g, 63%).

NMR (DMSO-d$_6$): δ1.33 (m, 22H), 3.20 (t, 4H), 3.75 (s, 3H).

Step (4) Preparation of 4-[(Cyclohexylmethyl)thio]-1,6-dihydro-2-(1,1-dimethylethyl)-6-oxo-5-pyrimidinecarbonitrile To a cooled (0° C.), stirred suspension of NaH (50% dispersion in mineral oil, washed with hexane, 1.49 g, 0.030 mol) in DMF (8 mL) was added a solution of t-butyl amidine (prepared in Step 1) (3.35 g, 0.025 mol) in DMF (10 mL) dropwise. The mixture was stirred at room temperature for 1 hour and then recooled to 0° C. A solution of methyl 3,3-bis(cyclohexylmethylthio)-2-cyano-2-propenoate (prepared in Step 3) (8.20 g, 0.022 mol) in DMF (25 mL) was added dropwise. The resulting solution was stirred at room temperature overnight. Water (100 mL) was added, the solution was filtered, and the filtrate was acidified with concentrated Hcl (10 mL). A precipitate formed and was collected by filtration. Trituration with acetone yielded an off-white powder (4.80 g, 71%), which was used without further purification.

NMR (DMSO-d$_6$): 1.30 (s, 9H), 1.38 (m, 11H), 3.15 (d, 2H).

Step (5) Preparation of t-butyl [[5-Cyano-6-[(cyclohexylmlethyl)thio]-2-(1,1-dimethylethyl)-4-pyrimidinyl]oxy]acetate To a cooled (0° C.), stirred suspension of NaH (50% dispersion in mineral oil, washed with hexane, 0.91 g, 0.019 mol) in DMF (10 mL) was added a solution of 4-[(cyclohexylmethyl)thio]-1,6-dihydro-2-(1,1-dimethylethyl)-6-oxo-5-pyrimidinecarbonitrile (prepared in Step 4) (4.80 g, 0.016 mol) in DMF (70 mL) dropwise. The mixture was stirred at room temperature for one hour. t-Butyl bromoacetate (3.05 mL, 0.019 mol) was added and stirring was continued overnight. Water (150 mL) was added, and the resulting precipitate was collected by filtration to give a white solid (6.05 g, 92%). The product was used without further purification.

NMR (CDCl$_3$): δ1.29 (s, 9H), 1.38 (m, 11H), 1.45 (s, 9H), 3.20 (d, 2H), 4.85 (s, 2H).

Step (6) Preparation of [[5-Cyano-6-[(cyclohexylmethyl)thio]-2-(1,1-dimethylethyl)-4-pyrimidinyl]oxy]acetic Acid A solution of t-butyl [[5-cyano-6-[(cyclohexylmethyl)thio]-2-(1,1-dimethylethyl)-4-pyrimidinyl]oxy]acetate (prepared in Step 5) (6.05 g, 0.014 mol) in trifluoroacetic acid (40 mL) was stirred at room temperature for 3 hours. The reaction mixture was concentrated to give a brown gum. Recrystallization from acetonitrile (3 times) yielded a white powder (2.1 g, 40%), m.p. 126°–128° C.

NMR (CDCl$_3$): δ1.30 (s, 9H), 1.40 (m, 11H), 3.16 (d, 2H), 4.98 (s, 2H).

IR (KBr): 2220, 1740 cm$^{-1}$.

UV (CH$_3$OH): 238 (29,600), 270 (10,000).

MS (m/e): 363, 224 (100%), 83.

Anal. Calcd.: C, 59.48; H, 6.93; N, 11.56%; Found: C, 59.57; H, 6.85; N, 11.50%.

EXAMPLE 2

(Process 2)

[[2-(5-Bromo-1-naphthalenyl)-5-cyano-6-[(1-naphthalenyl)methyl]-4-pyrimidinyl]oxy]acetic Acid

[(I): R$^1$=5-bromo-1-naphthalenyl; R=(1-naphthalenyl)methyl]

Step (1) Preparation of Methyl-2-(1-naphthalenyl)acetimidate Hydrochloride

To a cooled (0° C.), stirred mixture of 1-naphthylacetonitrile (9.2 g, 0.055 mol), methanol (5.0 mL, 0.124 mol), and ether (5 mL) was added acetyl chloride (5.2 g, 0.066 mol) dropwise. Stirring was continued for 30 minutes and the mixture was allowed to stand at room temperature for 60 hours. The resulting precipitate was collected by filtration, washed with ether, crushed with a mortar and pestle, and again washed with ether. The product was dried in vacuo to give a white crystalline solid (11.7 g, 91%), which was used without further purification.

NMR (CDCl$_3$): δ4.22 (s, 3H), 4.58 (s, 2H), 7.53 (m, 4H), 7.88 (t, 2H, J=6.0 Hz), 8.12 (d, 1H, J=7.0 Hz), 11.95 (br s, 1H).

Step (2) Preparation of Methyl-N-(5-bromo-1-naphthoyl)-2-(1-naphthalenyl)acetimidate According to the procedure of Soto et al, Synthesis, 483, (1983), to a stirred suspension of methyl-2-(1-naphthalenyl)acetimidate hydrochloride (prepared in Step 1) (11.7 g, 0.050 mol), in dry toluene (150 mL) was added triethylamine (11.5 g, 0.114 mol). 5-Bromo-1-naphthoyl chloride (13.4 g, 0.050 mol) was added in one portion and the resulting mixture was stirred at room temperature for 16 hours. The precipitated salt was removed by filtration and washed with toluene. The filtrate was concentrated in vacuo to give an orange oil (21.5 g, 100%) which was used without purification.

NMR (CDCl$_3$): δ3.88 (s, 3H), 4.27 (s, 2H), 7.12 (dd, 1H, J$_1$=12.0 Hz, J$_2$=6.0 Hz), 7.30 (m, 5H), 7.48 (d, 1H, J=7.0 Hz), 7.69 (d, 1H, J=6.0 Hz), 7.87 (m, 3H), 8.36 (d, 1H, J=7.0 Hz), 9.02 (d, 1H, J=7.0 Hz).

Step (3) Preparation of 2-(5-Bromo-1-naphthalenyl)-1,6-dihydro-4-[(1-naphthalenyl)methyl]-6-oxo-5-pyrimidinecarbonitrile To a stirred solution of sodium methoxide, freshly prepared from sodium (1.5 g, 0.065 mol) in methanol (75 mL), was added cyanoacetamide (4.2 g, 0.050 mol). After 2 minutes, methyl-N-(5-bromo-1-naphthoyl)-2-(1-naphthalenyl)acetimidate (21.6 g, 0.050 mol) was added. The resulting mixture was stirred at room temperature for 15 hours, then heated to reflux for 4 hours. After cooling to room temperature, the mixture was neutralized with H$_2$SO$_4$ (1.8 mL) and diluted with water. The product was collected by filtration, washed with water, and dried in vacuo to give a yellow solid (16.4 g, 71%), which was used without purification.

NMR (DMSO-d$_6$): δ4.63 (s, 2H), 7.07 (t, 1H, J=6.0 Hz), 7.51 (m, 4H), 7.80 (m, 5H), 7.97 (dd, 1H, J$_1$=6.0 Hz, J$_2$=2.0 Hz), 8.15 (dd, 1H, J$_1$=8.0 Hz, J$_2$=2.0 Hz), 8.34 (d, 1H, J=7.0 Hz).

Step (4) Preparation of t-Butyl [[2-(5-Bromo-1-naphthalenyl)-5-cyano-6-[(1-naphthalenyl)methyl]-4-pyrimidinyl]oxy]acetate To a stirred suspension of NaH (60% suspension in mineral oil, washed with hexane, 0.64 g, 16.1 mmol) in DMF (25 mL) was added a solution of 2-(5-bromo-1-naphthalenyl)-1,6-dihydro-4-[(1-naphthalenyl)methyl]-6-oxo-5-pyrimidinecarbonitrile (prepared in Step 3) (5.0 g, 10.7 mmol) in DMF (100 mL) at room temperature. After 30 minutes, t-butyl bromoacetate was added and stirring was continued for 18 hours. The reaction was quenched by the addition of water (10 mL) and the resulting mixture was partitioned between chloroform (200 mL) and water. The aqueous layer was extracted with chloroform (2×100 mL) and the combined organic layers were washed with water, brine, and dried (Na₂SO₄). The mixture was filtered through a short plug of Florosil and concentrated in vacuo to give a yellow solid (5.8 g, 48%). Recrystallization from acetonitrile/DMF gave 3.0 g of product which was used without further purification.

NMR (CDCl₃): δ1.42 (s, 9H), 4.84 (s, 2H), 5.00 (s, 2H), 6.95 (dd, 1H, $J_1=J_2=7.0$ Hz), 7.57 (m, 5H), 7.76 (d, 1H, J=6.0 Hz), 7.90 (m, 2H), 8.20 (m, 3H), 8.43 (d, 1H, J=8.0 Hz).

Step (5) Preparation of [[2-(5-Bromo-1-naphthalenyl)-5-cyano-6-[(1-naphthalenyl)methyl]-4-pyrimidinyl]oxy]acetic Acid A solution of t-butyl [[2-(5-bromo-1-naphthalenyl)-5-cyano-6-[(1-naphthalenyl)methyl]-4-pyrimidinyl]oxy]acetate (2.7 g, 4.6 mmol) in trifluoroacetic acid (40 mL) was stirred at room temperature for 6 hours. The solvent was removed in vacuo and the residue was triturated with ether. Recrystallization from ethanol (2 times) gave a white solid (1.4 g, 60%), m.p. 236°–237° C.

NMR (DMSO-d₆): δ4.89 (s, 2H), 5.16 (s, 2H), 7.05 (t, 1H, J=7.9 Hz), 7.52 (m, 4H), 7.73 (t, 1H, J=7.9 Hz), 7.86 (d, 1H, J=7.4 Hz), 7.90 (d, 1H, J=7.3 Hz), 7.97 (dd, 1H, $J_1=6.9$ Hz, $J_2=2.3$ Hz), 8.11 (d, 1H, J=7.3 Hz), 8.19 (d, 1H, J=8.7 Hz), 8.24 (d, 1H, J=8.7 Hz), 8.33 (d, 1H, J=8.4 Hz), 9.72 (br s, 1H).

IR (KBr): 3420, 2220, 1730 cm⁻¹.

Anal. Calcd.: C, 64.13; H, 3.46; N, 8.01%; Found: C, 64.09; H, 3.34; N, 8.06%.

We claim:

1. A compound of formula (I)

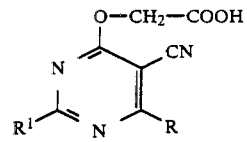

wherein R¹ is lower alkyl having 1 to 6 carbon atoms, cyclo(lower)alkyl having 3 to 6 carbon atoms, phenyl, halogen substituted phenyl, phenylmethyl, naphthalenyl, halogen substituted naphthalenyl, or thienyl; R is —S—R² wherein R² is lower alkyl having 1 to 6 carbon atoms, lower cycloalkylmethyl having 4 to 7 carbon atoms, phenylmethyl, or halogen substituted phenylmethyl; or R is R³ wherein R³ is lower alkyl having 1 to 4 carbon atoms, phenyl, or 1-naphthalenylmethyl; or a pharmaceutically acceptable salt thereof.

2. A compound according to claim 1 wherein R¹ is 1-methylethyl, 1,1-dimethylethyl, propyl, 2,2-dimethylpropyl, phenyl, 4-bromophenyl, naphthalenyl, 5-bromonaphthalenyl, or 2-thienyl; R is —S—R² wherein R² is methyl, 1-methylethyl, hexyl, cyclohexylmethyl, phenylmethyl, 4-bromophenylmethyl, or 4-bromo-2-fluorophenylmethyl; or R is R³ wherein R³ is methyl, 1-methylethyl, phenyl, or 1-naphthalenylmethyl; or a pharmaceutically acceptable salt thereof.

3. A compound according to claim 2 wherein R¹ is 1,1-dimethylethyl or 5-bromonaphthalenyl; R is —S—R² wherein R² is methyl, hexyl, cyclohexylmethyl, or phenylmethyl; or R is R³ wherein R³ is 1-naphthalenylmethyl; or a pharmaceutically acceptable salt thereof.

4. The compound according to claim 3 designated [[5-cyano-6-[(cyclohexylmethyl)thio]-2-(1,1-dimethylethyl)-4-pyrimidinyl]oxy]acetic acid or a pharmaceutically acceptable salt thereof.

5. The compound according to claim 3 designated [[2-(5-bromo-1-naphthalenyl)-5-cyano-6-[(1-naphthalenyl)methyl]-4-pyrimidinyl]oxy]acetic acid or a pharmaceutically acceptable salt thereof.

6. A pharmaceutical composition for relieving the symptoms of neuropathy, nephropathy, retinopathy, or cataracts in a diabetic mammal, which comprises an effective amount of a compound of claim 1 and a pharmaceutically acceptable carrier.

7. A method of relieving the symptoms of neuropathy, nephropathy, retinopathy, or cataracts in a diabetic mammal, which comprises administering to said mammal an effective amount of a compound of claim 1.

* * * * *